US006730201B1

(12) United States Patent
Kuhlman et al.

(10) Patent No.: US 6,730,201 B1
(45) Date of Patent: May 4, 2004

(54) ELECTRONIC TONGUE

(75) Inventors: Kimberly Kuhlman, Shadow Hills, CA (US); Martin G. Buehler, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 181 days.

(21) Appl. No.: 09/670,902

(22) Filed: Sep. 28, 2000

Related U.S. Application Data

(60) Provisional application No. 60/156,643, filed on Sep. 28, 1999.

(51) Int. Cl.[7] .................. G01N 27/333; B05D 3/00
(52) U.S. Cl. .................. 204/416; 204/418; 427/2.13
(58) Field of Search .................. 204/403.05, 403.03, 204/416, 418, 409, 419; 427/2.13

(56) References Cited

U.S. PATENT DOCUMENTS

| 4,404,065 A | * | 9/1983 | Matson ..................... 205/780.5 |
| 5,183,549 A | * | 2/1993 | Joseph et al. ............... 204/415 |
| 5,310,469 A | * | 5/1994 | Cunningham et al. . 204/403.09 |
| 5,571,396 A | * | 11/1996 | Cormier et al. .............. 204/418 |
| 5,830,338 A | | 11/1998 | Seto et al. ................... 204/416 |
| 5,840,168 A | | 11/1998 | Chaniotakis et al. ........ 204/416 |
| 5,891,398 A | | 4/1999 | Lewis et al. ............. 422/82.02 |
| 5,916,425 A | * | 6/1999 | Leader et al. .......... 204/403.01 |

OTHER PUBLICATIONS

Lavigne et al., "Solution–Based Analysis of Multiple Analytes by a Sensor Array: Toward the Development of an Electronic Tongue", J. Am. Chem. Soc., vol. 120, No. 25, pp 6429–6430, Jul. 1, 1998.

Wood et al., "They've got it licked", New Scientist, p 10, Jul. 18, 1998.

Winquist et al., "Monitoring of freshness of milk by an electronic tongue on the basis of voltammetry", Meas. Sci. Technol., pp 1937–1946, 9 (1996), month unknown.

* cited by examiner

Primary Examiner—Alex Noguerola
(74) Attorney, Agent, or Firm—Fish & Richardson P.C.

(57) ABSTRACT

An ion selective electrode (ISE) array is described, as well as methods for producing the same. The array can contain multiple ISE which are individually electronically addressed. The addressing allows simplified preparation of the array. The array can be used for water quality monitoring, for example.

11 Claims, 5 Drawing Sheets

ELECTRONIC TONGUE

This application claims the benefit of U.S. Provisional Application No. 60/156,643, filed Sep. 28, 1999.

GOVERNMENT INTEREST

The invention described herein was supported in part by NASA contract NAS7-1407, task order 10486. The Government has certain rights in this invention.

FIELD OF THE INVENTION

The invention relates to sensors for the measurement of chemical species. More particularly, the invention relates to simultaneous electrochemical detection of chemical species using sensors on a substrate.

BACKGROUND OF THE INVENTION

Ion selective electrodes (ISE) are used in the analytical determination of basic chemical parameters of samples. ISE are able to meet strict requirements for low sample mass, rapid and continuous measurement that are imposed by operation in remote environments, such as onboard spacecraft. Generally, ISE allow the elimination of time-consuming sample preparation steps such as filtration, weighing and distillation, resulting in fewer systematic measurement errors, better standard deviation, and more accurate measurements.

ISE known in the art include recently developed carrier-based polymeric membrane ISE, the key components of which include: a lipophilic complexing agent, known as an ionophore, capable of reversibly binding an analyte; and a solvent polymeric membrane composed of a high viscosity, water-immiscible liquid. Polymer-based ISE using $Ag^+$ instead of $Cl^-$ are known to produce more stable potentials where there are changes in pressure, concentration and temperature.

SUMMARY OF THE INVENTION

The deposition and/or modification of individual ISE sensors in an array by individually electronically addressing each ISE sensor, and using processes to dope the electrolyte with appropriate ions, is described herein. Such techniques allow an assembly of ISE arrays to be constructed that enable the use of neural nets and pattern recognition software, thereby increasing the quantity and quality of information obtained from the sensors.

The devices and processes described herein provide a number of advantages. For example, the devices allow simultaneous measurement of the presence of particular chemical species in a sample, and can give measurement of particular physical properties of the sample. Among these are identity and quantification of chemical species. The devices can monitor pH, the presence of inorganic species, organic species, gases, as well as monitoring conductivity and oxidation-reduction potential (ORP) of samples. The devices are also able to determine biological signatures of organisms or residual chemical mixtures characteristic of the presence of organisms.

The devices contain sensors which are made to a surface area density of up to 10 times that of conventional sensors, enabling more data collection. The devices are able to be constructed at lower cost than conventional chemical sensor arrays. The devices are highly portable, and suitable for use by individual consumers as well as by industrial entities.

The use of such devices in chemical, medical and pharmaceutical laboratories carries particular advantages, such as on-line process monitoring, industrial water quality monitoring, monitoring of biologically essential fluids in remote locations such as on board spacecraft, and the ability to conduct biological signature analysis for planetary systems, or on earth.

The processes used to create such devices represent the first application of directed deposition of spatially resolved species by electrical means. These processes also have the particular advantage of not using maskless processes to personalize the characteristics of individual sensors in the array. Maskless processes eliminate costly and environmentally undesirable steps such as photolithography, micro- or nanopipetting, or ink jetting of dopant molecules.

The devices described herein also include novel circuitry and methods of monitoring and carrying out deposition processes. The novel circuitry enables the use of potentiometric or galvanometric monitoring and deposition. These two modes can be chosen according to the wishes of the operator, and can be alternated when desired. Alternatively, the process can be switched by an automated switch, according to preset parameters.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

A multi-sensor array is described, which simultaneously measures properties of a variety of chemical species in a sample. The device is an integrated, rugged, reliable, low mass/power, analytical device which can identify and quantitatively determine basic sample quality parameters. Processes used to fabricate these devices include local doping of a polymer, and optionally and desirably, a gel layer, by specific ionophores, which are attracted toward, and driven into, the polymer, and optionally, the gel, at particular locations using an electric field.

The sample sensor described herein can be fabricated using hybrid microelectronic co-fired ceramic techniques to form a ceramic substrate. The substrate can comprise other materials, and can be made of any suitably resilient, and electrically non-conductive material. In some embodiments, the substrate comprises multiple layers, and can include as many as seven layers or more. The substrate is covered at least in part by other layers: at least one polymer layer, optionally and desirably, at least one gel layer, and at least one protective layer.

Figure 1:
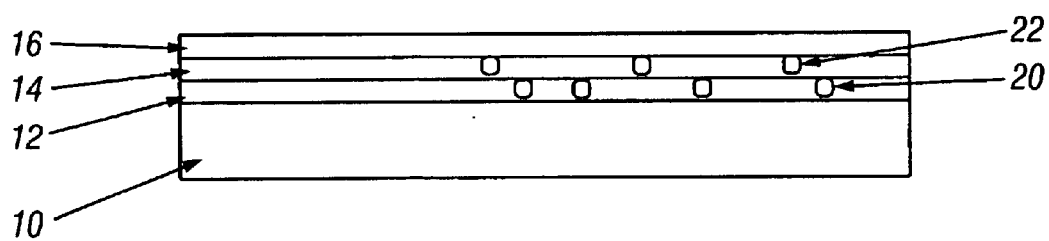
FIG. 1 is a schematic diagram of a sensor structure according to a particular embodiment.

A particular embodiment of such a layered structure is shown in FIG. 1, which shows substrate layer 10, gel layer 12, polymer layer 14, and protective layer 16. FIG. 1 also shows ionophore 20 in gel layer 12, and ionophore 22 in polymer layer 14, which are described below in detail.

A gel layer is optionally and desirably screen-printed onto at least a portion of the surface of the resulting ceramic substrate. Suitable gels are hydrated gels, which form an interface between the electrode and the polymer layer of the layered structure. Gels which are suitable for use in the devices and methods described herein include, for example, hydrated gels and gels which include salts. Salts in the gels for use in these devices are used to facilitate contact to silver electrodes. Gels can also take the form of thin glasses, including amorphous glasses.

Screen-printing processes are described in such references as R. J. Hannemann, "Semiconductor Packaging: A Multidisciplinary Approach," Wiley, (1994), Chapter on Hybrid Microelectronics.

The resulting gel layer can be desirably directly doped with an ionophore. The direct doping proceeds directly subsequent to the previous screen-printing step.

Alternatively, the gel layer can be indirectly doped during the polymer doping step. The doping of gel (and/or polymer) layers involves selective doping of each ISE by using an electric field to focus the dopants to a specific area on the gel or polymer layer. The dopants (that is, the ionophores) are present in a solution or suspension, and added to the layer to be doped, for example the polymer layer, or the optionally present gel layer. The liquid phase can be any liquid phase which can be used with an electrically driven deposition process. In preferred embodiments, the liquid of the dopant solution can include water, and in more preferred embodiments, the liquid is substantially water. The concentrations of ionophores can be chosen to provide sufficient discrimination of ionic species when deposited. An upper limit to ionophore concentration at a deposition site is generally determined by the self-screening effect of the ionophore which would prevent further deposition by electrical means. The concentration of ionophore in a dopant solution can be from about 1 $\mu$M to about 5 M.

Ionophores for use in the methods and devices used herein are those which can be directed by an electric or magnetic field, for example, those ionophores which are charged or are polarizable. Commercially available ionophores have been reported for a wide range of species, including inorganic cations, inorganic anions, organic cations, organic anions, and neutral species. Inorganic cations for which ionophores have been reported include protons, lithium, sodium, potassium, rubidium, cesium, beryllium, magnesium, calcium, strontium, barium, molybdenum, iron$^{III}$, copper$^{II}$, silver, zinc, cadmium, mercury, tellurium, bismuth, lead, uranium, samarium, ammonium ions and others. Inorganic anions for which ionophores have been reported include carbonate, hydrogen carbonate, thiocyanate, nitroxy, hydroxy, phosphate, sulfite, sulfate, chloride, selenium oxide, iodide, and others. Organic cations for which ionophores have been reported include 1-phenylethylamine, 1-(1-naphthyl)-ethylamine, ephedrine, norephedrine, pseudoephedrine, amphetamine, propanolol, amino acid methyl esters, $\alpha$-amino-$\epsilon$-caprolactam, amino acid amides, benzyl amine, alkyl amines, dopamine, mexiletine, local anasthetics (including procaine, prilocaine, lidocaine, bupivacaine, lignocaine, and others), the herbicides diquat and paraquat, tetramethyl- and tetraethylammonium, guanidine, metformin, phenformin, creatinine, protamine, and others. Organic anions for which ionophores have been reported include salicylate, phthalate, maleate, 2-hydroxybenzhydroxamate, nucleotides, hepartin, and others. Neutral species for which ionophores have been reported include carbon dioxide, oxygen, ammonia, and others.

Ionophores considered desirable for the purposes of the devices described herein have a substantially linear response to analytes in the range of from about $10^{-8}$ M to about 10 M, or from about $10^{-6}$ M to about 1 M. Ionophores can be polyethers, crown ethers, polypeptides, chelating agents generally, including phosphonic acids, polyphosphates, aminocarboxylic acids, 1,3-diketones, hydroxycarboxylic acids, polyamines, aminoalcohols, aromatic heterocyclic bases, phenols, aminophenols, oximes, Schiff bases, tetrapyrroles, thiols, xanthates, and other sulfur compounds, polymers such as polyethylenimine, polymethacryloylacetone, poly(acrylic acid), and compounds containing such moieties or combinations of such moieties. Ionophores for use in the devices and methods described herein include lipophilic complexing agents capable of reversibly binding an analyte. Examples of useful ionophores are those commercially available from A. G. Scientific (San Diego, Calif.), for example, calixarenes, isoxazolidinone such as 4-Amino-3-isoxazolidinone, methane sulfonates, and valinomycins.

Doping of the layers of the device relies on the principles of electrodiffusion and electroosmosis. The doping proceeds according to the steps described herein. The ISE are individually electronically addressed. Then electromigration or electropolymerization are used to dope the gel electrolyte with the appropriate ion, or the sensing polymer membrane with the selective ionophore.

Figure 2:
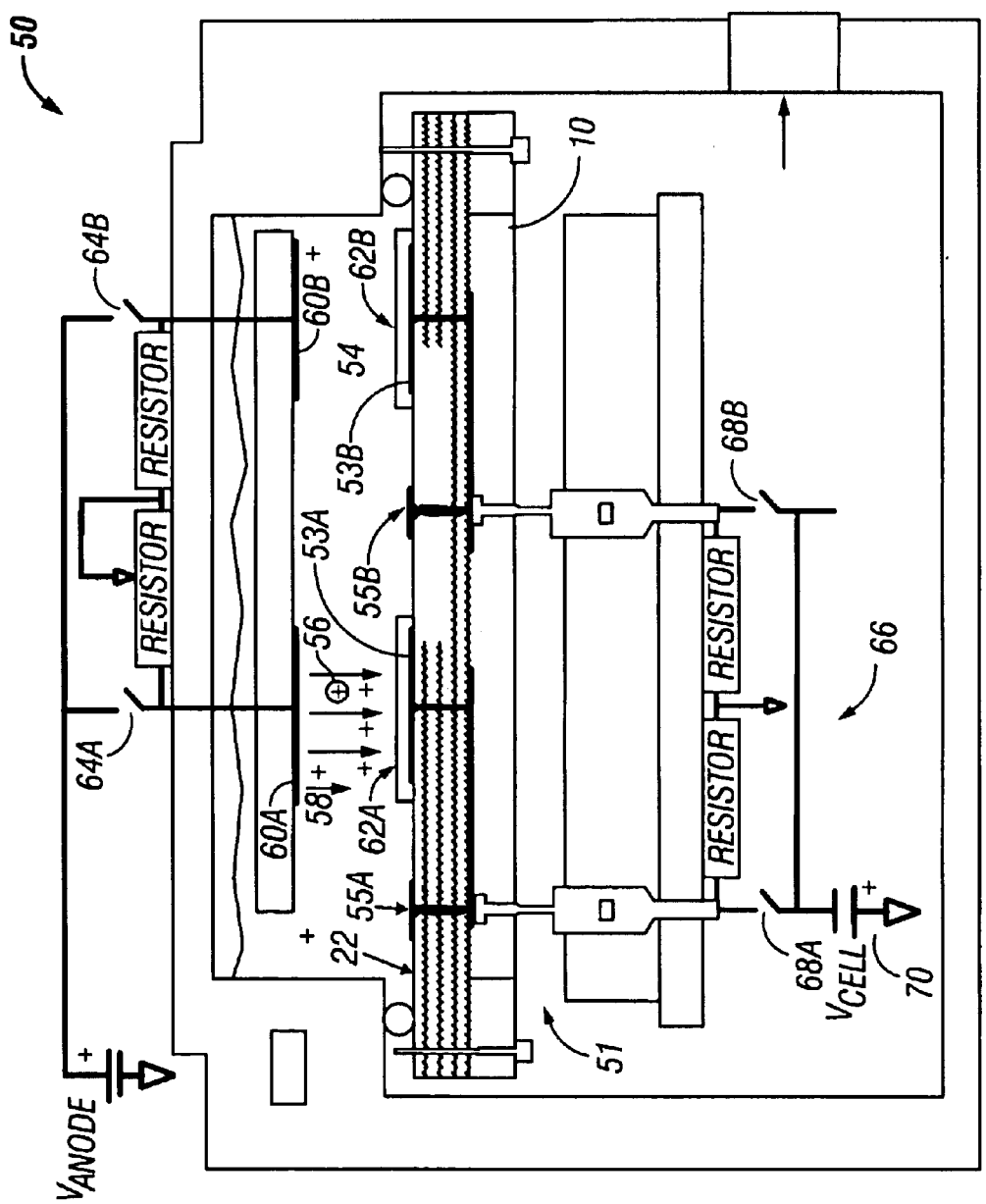
FIG. 2 is a schematic diagram of a deposition chamber for use with particular methods of deposition.

In general the doping process proceeds as follows, and reference is made to FIG. 2. FIG. 2 shows deposition chamber 50, which houses sensor array 51 including substrate 10. Substrate 10 has electrodes 52, with upper electrode surfaces 53 passing through it to an upper surface 22 of substrate 10. Electrodes can be of any conductive material used for such purposes, and in preferred embodiments, are silver electrodes. Electrolyte 54 contains doping ions 56 which can be positively or negatively charged. Application of electric field 58 (depicted by downward directed arrows) between first electrode surface 53A and first split anode 60A drives doping ions 56 into first gel layer 62A. Reference electrodes 55A and 55B are also shown. The doping of first electrode surface 53A is carried out by closing switch 64A to complete the circuit.

To dope second electrode surface 53B, the electrolyte solution can be replaced by another electrolyte solution with a different or same doping ion. The doping of second electrode 53B is not carried out until switch 64B is closed to complete the circuit. Associated electronics 66, including switches 68A and 68B on the opposite side of the substrate are used to complete the circuits for the doping of first and second electrodes, respectively.

The general process proceeds as follows. After sensor array 51 is mounted in the chamber, doping ions 56 in electrolyte 54 are directed to a particular electrode by connecting potential $V_{cell}$ 70 to first electrode 53A (reference electrodes are in electrical communication with electrodes 53A and 53B). After doping the first gel 62A, electrolyte 54 containing doping ion 56 is removed and a different electrolyte is introduced into the chamber and is deposited directedly to second electrode 53B. This process allows the individual doping of each electrode in the array with a different ionophore. The chamber has a split anode, so that the electric field exists substantially only at the electrode being doped. This minimizes depopulation of electrodes previously doped.

In particular embodiments, the gel layer is doped during the polymer layer doping step described below. That is, the dopant can be added to the polymer layer and made to enter the gel layer by the techniques described herein and direct doping of the gel layer after screen-printing can be made unnecessary.

The gel layer is then screen-printed with a polymer layer. The screen printing of the polymer layer proceeds as described above with reference to the polymer layer.

The resulting polymer layer is then doped with an ionophore. This ionophore can be the same as, or different than, the ionophore of the gel layer. Combination of ionophores can dramatically increase the selectivity of detection, by effectively multiply screening analyte species. As described above, the doping of the gel layer can be indirectly accomplished at this stage by doping of the polymer layer and application of an electric field which populates the gel layer with dopant.

Polymers which are useful for making polymer layers in the devices and methods described herein are electoactivated PVC-like polymers, and other materials as disclosed in Skoog and Leary, "Principles of Instrumental Analysis" Harcourt-Brace, (1992), Chapters 19, 20, 21 and 22. Additional components may be present in the polymer layer, such as plasticizers, and compatibilizers, and other materials typically used to improve polymer qualities.

Finally, a protective layer is screen-printed onto the polymer layer. Alternatively, screen-printing can be used to spot-print a protective layer over the individual ISE without forming a complete layer. Individual protective layers can be printed over each ISE after it is doped, to further minimize depopulation of doped ISE during subsequent ISE doping steps. Materials which can form protective layers which are suitable for the devices and methods described herein include any resilient materials which are non-conductive, and non-contaminating of the electrolyte which will be incontact with them. The protective layer should be porous in order that analytes are able to penetrate the protective layer.

Figure 3:
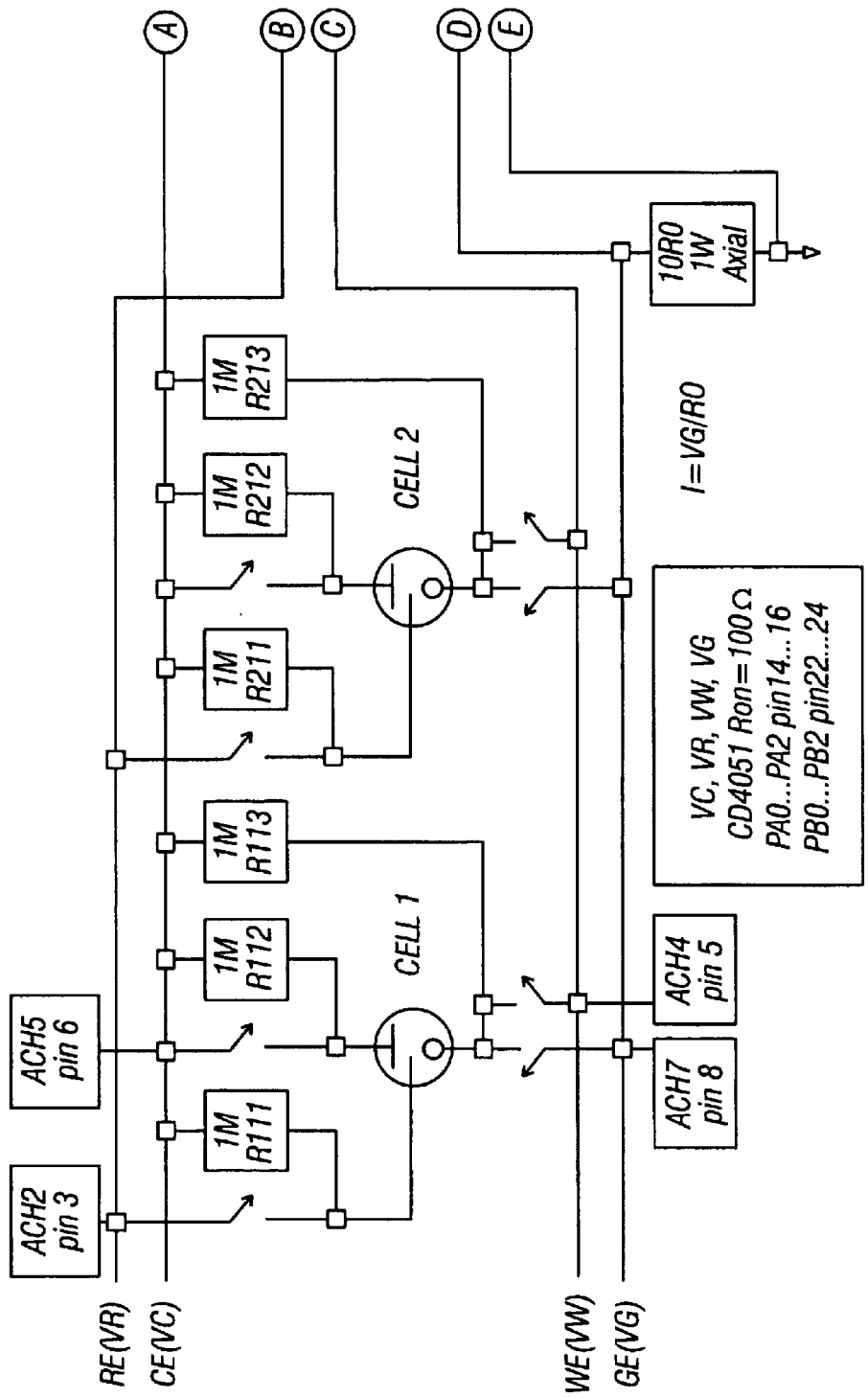
FIG. 3 is a schematic diagram of a particular microelectronic circuit for use with particular methods of deposition.
Figure 3:
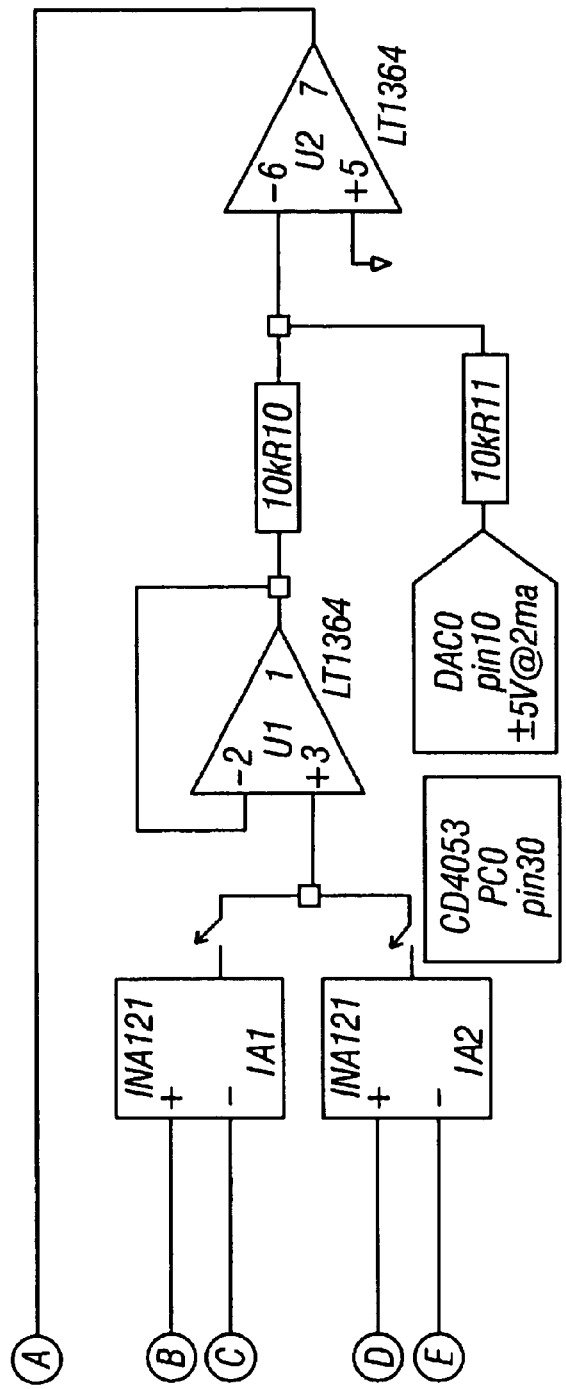

The sensor array is electrically attached to microelectronics which are used to measure the ISE potentials selectively using multiplexers. A suitable microelectronic circuit is shown in FIG. 3. FIG. 3 shows cell addressing and biasing circuitry, an on-chip themometer useful for deposition of ionophores in a sensor array, for example, as described herein. The electronic circuit is equipped to carry out either potentiometric or galvanometric monitoring and/or deposition, for example, in conjunction with the deposition chamber described above, or with other deposition chambers within the scope of the appended claims. The choice of potentiometric or galvanometric monitoring and/or deposition can be made by opening or closing switches shown in FIG. 3 and labeled as CD4053. Leads labeled RE, CE, WE and GE are for the reference electrode, counter electrode (split anode), working electrode, and galvanometric electrode respectively. The reference electrode and galvanometric electrode are the same physical electrode (53A and 53B in FIG. 2), but can operate in potentiometric or galvanometric mode, as described herein. The reference electrode is depicted in FIG. 3 as a lead entering cell 1 or cell 2 from the left. The working electrode is depicted in FIG. 3 as a lead entering from the bottom of cell 1 or cell 2, and the counter electrode is depicted as entering from above. Kelvin junctions are depicted as connecting, for example, pin 8 and pin 5 to cell 1 in FIG. 3.

The alternation between potentiometric and galvanometric monitoring and/or deposition can be made with reference to changes in voltage or current, respectively. The process can be automated, so that when the rate of change of voltage reaches a particular level during potentiometric monitoring and/or deposition, desirably a particularly low level, a change to galvanometric monitoring and/or deposition can be made by a computer or other mechanical or electronic device activating a switch. Alternatively, when the rate of change of current reaches a particular level during galvanometric monitoring and/or deposition, desirably a particularly low level, a change to potentiometric monitoring and/or deposition can be made by a computer or other mechanical or electronic device activating a switch. The monitoring and/or deposition can either begin as potentiometric or galvanometric, depending on the polymer, the gel, or the ionophore being deposited. It is within the skill of one in the art to determine the proper method of monitoring and/or deposition to use initially. The switch point to the other method of monitoring and/or deposition can occur when the rate of change of either potential or current reaches a value less than, for example, about 20% per minute, or less than about 10% per minute, or less than about 5% per minute, or less than about 2% per minute, or less than about 0.5% per minute.

The potentials are evaluated using analog-to-digital converters and the results are transmitted to a computer equipped with appropriate data collection and analysis software. The results are analysed to identify the type and amount of ionic concentration in the sample. Multiple sensors for the same ion can be implemented in the arrays described herein, as well as sensors for multiple ions. Accurate dynamic recalibration of individual sensors is made possible by these features, as well as quantification of the ionic species present. Self-diagnosis of performance in situ and dynamic recalibration are highly desirable for treatment of changing operation conditions and shifting baselines in the individual ISE sensors. The sensor arrays described herein possess not only the ability to recognize the appearance of a target sample component, but also provide real-time continuous monitoring of specified concentration levels. Potentiometric sensors have been shown to be analyzable by a nonlinear multivariate calibration regression technique. The coefficients of the Nikolskii-Eisenman equation are optimized according to this technique, and a description of the response of an individual ISE when part of a larger array of sensors is obtained, as described in Hartnett et al., *Anal. Chem.*, 69, (1997) 1:909–18.

The measured potential of the $j^{th}$ electrode for the $i^{th}$ sample ($E_{ij}$), is described by the simple equation:

$$E_{ij}=E_j^O+S_j \log\{a_{ik}+\Sigma_{l \neq k}k_{jkl}^{pot}a_{il}^{3k/3l}\}$$

where $E_j^O$ is the standard cell potential for the ISE, and $S_j$ is the slope or change in the potential of the electrode per decade change in the activity of the primary ion in the absence of interfering species. The activity of the primary ion k in the $i^{th}$ sample is $a_{sk}$ and the interfering ions l are given by $a_{il}$. This technique is used with large array elements to calculate individual activities and correlate them with the actual activities of model solutions.

Simplex optimization, genetic algorithms and pattern recognition analysis have been combined with fuzzy logic and neural networks in the investigations of routines for use with data analysis for multisensors, as described in Kress-Rogers, "Handbook of Biosensors and Electronic Noses: Medicine, Food, and the Environment" CRC Press, Inc., Boca Raton, Fla., (1997), and Hartnett et al., (1997).

The device can be fabricated to determine the presence and semi-quantitatively determine the amount of from 10 to 100 organic and inorganic analytes in a sample. In preferred embodiments, the device can be used to determine more than 20 analytes, and in more preferred embodiments, more than 40 analytes, simultaneously and continuously.

In some preferred embodiments, the sample is a water-containing sample. In particular more preferred embodiments, the sample includes water as a major component of the sample. Such samples allow the device described herein to operate as an in-line device for the determination of water quality, and can give useful results within hours, rather than the day-long time scale of presently available monitors.

The device can be used to analyse blood or urine samples.

The device, when established to operate with aqueous samples, can be used to carry out the in situ analysis of life forms and the chemical signatures of extant or past life. The changes due to metabolic activity such as the consumption of nutrients or the production of waste can be monitored by comparison against a background chemical composition, structure and behavior.

The invention will be further described in the following examples, which do not limit the scope of the invention described in the claims.

EXAMPLES

Example 1
Preparation of a 9-Element ISE Sensor

A 9-element ISE sensor is fabricated on a 45 mm diameter ceramic substrate. The substrate is a co-fired ceramic in which electrodes are formed using screen-printing technology. The sensor is inserted into a socket mounted on a printed circuit board containing custom-made electronic circuitry according to FIG. 3, designed to collect signal from each ISE.

ISE fabrication involves screen-printing gel, polymer and protective layers. After the sensor is mounted in the chamber, an electrolyte containing ionophores fills the chamber. Then the ionophores are directed to a particular electrode by connecting the potential Vcell to the desired electrode. After doping the gel, the ionophore is removed and a different ionophore is introduced into the chamber and directed electrostatically to a new electrode. This process allows individual doping of each electrode in the array with a different ionophore. After the gel is doped, the polymer layer is screen-printed and doped by the same procedure used to dope the gel.

The chamber has a split anode, so that the electric field exists only at the electrode being doped. This prevents depopulation of electrodes previously doped. After polymer doping, a protective layer is screen printed over each electrode.

Example 2
Construction of an In-line Water Quality Monitor

Figure 4:
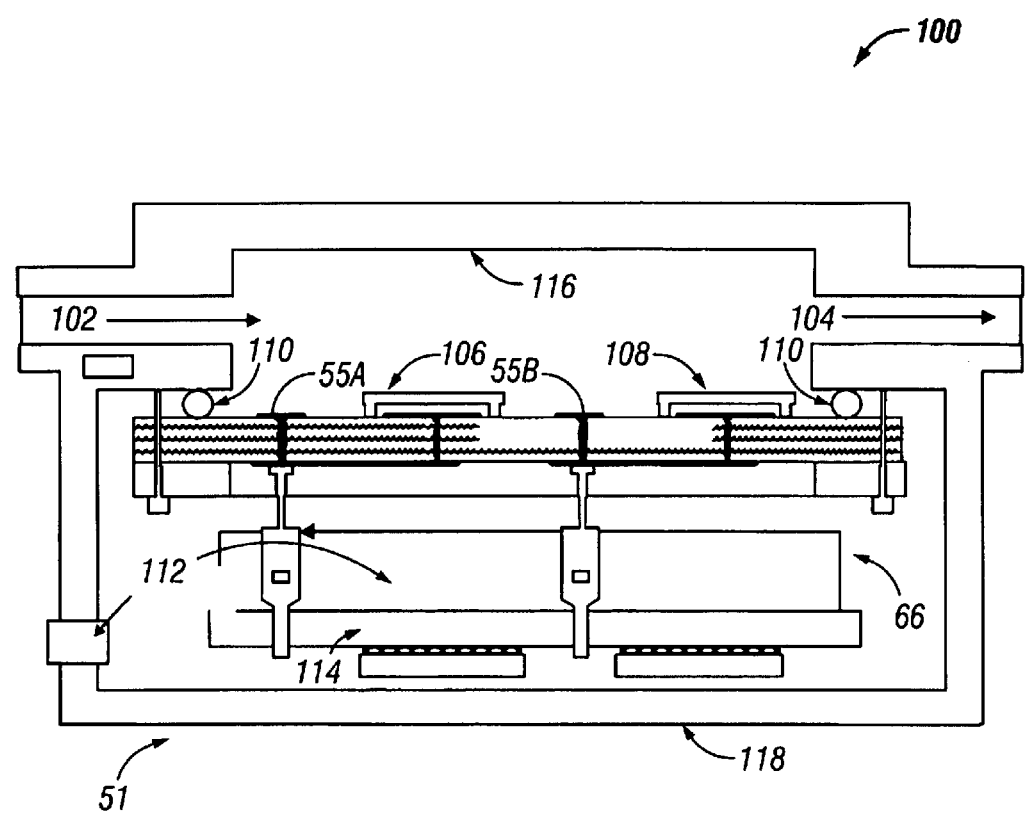
FIG. 4 is a schematic diagram of a particular in-line water quality sensor.

After fabrication of a sensor array according to Example 1, the sensor is mounted in an on-line water quality housing shown in FIG. 4. This housing contains the electronics, for example those depicted in FIG. 3, so that the ISE can be measured using a serial interface to a computer. FIG. 4 shows a cross-sectional view of in-line water quality monitor 100, inlet 102, outlet 104, sensor array 51, reference electrodes 55A and 55B, electronics array 66, first ion selective electrode 106, and second ion selective electrode 108, O-ring 110, ZIF socket 112, printed circuit board 114, lid 116, and housing 118. Water to be sampled enters inlet 102 and is sampled by first and second ion selective electrodes 106 and 108. Analyte in the water (not shown) interacts with ionophores (not shown, but deposited in polymer and/or gel layers proximate ion selective electrodes) present proximate ion selective electrodes, altering current and or potential. The alterations are measured by the electronics array 66, and the signals generated by the electronics array are input into a computer with appropriate data analysis software for monitoring.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A sensor array for the determination of at least one analyte in a liquid sample, the array comprising:
   a substrate, comprising a plurality of reference electrodes and a plurality of qel-coated electrodes, each of the gel-coated electrodes coated with a gel layer, the gel layer at least partially coated with a polymer layer, wherein each gel layer comprises a first ionophore and each polymer layer comprises a second ionophore and a protective layer at least partially coating the polymer layer.

2. The array of claim 1, wherein the ionophore in each gel layer and each polymer layer of one gel-coated electrode is different from any other ionophore in the array of gel-coated electrodes.

3. A water quality sensor comprising: the array of claim 1 in fluid communication with the liquid sample, and wherein the electrodes are in electrical communication with circuitry for determination of a property of at least one analyte present in the liquid sample.

4. The sensor of claim 3, wherein the property determined by the sensor is the presence of at least one analyte.

5. The sensor of claim 3, wherein the sensor determines properties of at least 10 analytes in a fluid sample.

6. The sensor of claim 3, wherein the sensor determines properties of at least 40 analytes in a fluid sample.

7. The sensor array of claim 1, wherein the first ionophore and the second ionophore are the same.

8. The sensor array of claim 1, wherein the first ionophore and second ionophore are different.

9. A sensor array made by a process comprising:
   providing a substrate comprising a plurality of reference electrodes and a plurality of gel-coated electrodes, wherein each of the gel-coated electrodes are coated with a gel layer;
   contacting each Of the gel layers with a different charged or polarizable ionophore;
   applying an electric field to each gel layer sufficient to migrate the ionophore into the gel layer;
   coating each gel layer comprising the ionophore with a polymer layer comprising the same or a different ionophore; and
   coating each polymer layer with a protective layer.

10. The sensor array of claim 9, wherein each gel layer is contacted simultaneously with the different charged or polarizable ionophore.

11. The sensor array of claim 9, wherein the electric field is simultaneously applied to each gel layer.

* * * * *